US006475480B1

(12) United States Patent
Mehtali et al.

(10) Patent No.: US 6,475,480 B1
(45) Date of Patent: Nov. 5, 2002

(54) USE OF ADENOVIRAL E4 READING FRAMES TO IMPROVE EXPRESSION OF A GENE OF INTEREST

(75) Inventors: Majid Mehtali, Illkirch-Graffenstaden (FR); Monica Lusky, Freiburg (DE)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/348,049

(22) Filed: Jul. 6, 1999

(30) Foreign Application Priority Data

Jul. 7, 1998 (EP) ............................................. 98401722
Nov. 13, 1998 (EP) ............................................. 98402825

(51) Int. Cl.$^7$ ........................ A01N 63/00; A01N 43/04; C12N 15/00; C12N 7/00; C12N 15/63
(52) U.S. Cl. ..................... 424/93.2; 514/44; 435/320.1; 435/235.1; 435/440; 435/455; 435/456
(58) Field of Search ........................... 435/320.1, 235.1, 435/440, 455, 456; 514/44; 424/93.2

(56) References Cited

U.S. PATENT DOCUMENTS

| | | | |
|---|---|---|---|
| 5,670,488 A | | 9/1997 | Gregory et al. ................ 514/44 |
| 5,756,283 A | * | 5/1998 | Wilson et al. ................... 435/5 |
| 5,981,275 A | * | 11/1999 | Armentano et al. ...... 435/320.1 |
| 6,093,567 A | * | 7/2000 | Gregory et al. .......... 435/320.1 |
| 6,100,086 A | | 8/2000 | Kaplan et al. ............ 435/320.1 |

FOREIGN PATENT DOCUMENTS

| | | | |
|---|---|---|---|
| WO | WO94/12649 | | 6/1994 |
| WO | WO96/13596 | | 5/1996 |
| WO | WO 98/21350 | * | 5/1998 |
| WO | WO98/46779 | | 10/1998 |
| WO | WO98/46781 | | 10/1998 |

OTHER PUBLICATIONS

Eck et al. Gene–Based Therapy. Goodman & Gilman's The Pharmacological Basis of Therapeutics, 9th edition, Chapter 5, pp. 77–101. 1996.*
Verma et al. Gene Therapy—Promises, Problems, and Prospects. Nature, vol. 389, pp. 239–242. Sep. 18, 1997.*
Yeh et al. Efficient Dual Transcomplementation of Adenovirus E1 and E4 Regions from a 293–Derived Cell Line Expressing a Minimal E4 Functional Unit. Journal of Virology, vol. 70, pp. 559–565. Jan. 1996.*

XP–002086859: D. Armentano et al, "Effect of the E4 Region on the Persistence of Transgene Expression from Adenovirus Vectors", *Journal of Virlogoy* (Mar. 1997), p. 2408–2416.

XP–002086860: D. Brolough et al., "Activation of Transgene Expression by Early Region 4 Is Responsible for a High Level of Persistent Transgene Expression from Adenovirus Vectors in Vivo", *Journal of Virology* (Dec. 1997), p. 9206–9213.

XP–002086861: P. Yeh et al., "Advances in Adenoviral Vectors: From Genetic Engineering to Their Biology", *The FASEB Journal* (Jul. 1997) vol. 11, p. 615–623.

XP–002086862: V. Mautner et al., "Enteric Adenovirus Type 40: Complementation of the E4 Defect in Ad2 di808", *Virology* (1991) vol. 183, p. 433–436.

XP–002086863: K. Leppard, "E4 Gene Function in Adenovirus, Adenovirus Vector and Adeno–associated Virus Infections", *Journal of General Virology* (1997) vol. 78, p. 2131–2138.

XP–002123650: M. Lusky et al., "Regulation of Adenovirus–Mediated Transgene Expression by the Viral E4 Gene Products: Requirement for E4 ORF3", *Journal of Virology* (Oct. 1999), p. 8308–8219.

* cited by examiner

Primary Examiner—Deborah J. Reynolds
Assistant Examiner—Eleanor Sorbello
(74) Attorney, Agent, or Firm—Burns, Doane, Swecker & Mathis, L.L.P.

(57) ABSTRACT

Described are recombinant adenoviral vectors retaining sufficient E4 sequences to improve the expression and/or persistence of expression of a gene of interest. Furthermore, the invention describes the use of a polynucleotide encoding one or more ORF(s) of the E4 region of an adenovirus selected from ORF1, ORF2, ORF3, ORF4, ORF3/4, ORF6/7, ORF6 and ORF7 taken individually or in combination, to improve the expression and/or persistence of expression of a gene of interest operably linked to regulatory elements and inserted into an expression vector. Finally, a host cell, a composition, an infectious viral particle comprising such a polynucleotide or adenoviral vector, a method for preparing said viral particle as well as their therapeutic use are described.

52 Claims, No Drawings

USE OF ADENOVIRAL E4 READING FRAMES TO IMPROVE EXPRESSION OF A GENE OF INTEREST

This application claims priority under 35 U.S.C. §§119 and/or 365 to EP 98 40 1722,8 filed, in Europe on Jul. 7, 1998 and EP 98 40,2825,8 filed in Europe on Nov. 13, 1998; the entire contents of which are hereby incorporated by reference.

The present invention relates to a recombinant adenoviral vector deleted of all or part of the E1 region and a part of the E4 region but retaining sufficient E4 sequences to improve expression and/or persistence of expression of a recombinant gene in a host cell or organism. Furthermore, it relates to the use of adenoviral E4 open reading frames (ORFs) to improve expression or persistence of expression of a recombinant gene inserted in an expression vector. Finally, the invention relates to a method for preparing a viral particle, a cell, a pharmaceutical composition comprising such vectors as well as their therapeutic or prophylactic use. The invention is of very special interest in relation to prospect for gene therapy, in particular in men.

Gene therapy can be defined as the transfer of genetic material into a cell or an organism to treat or prevent a genetic or acquired disease. The possibility of treating human disorders by gene therapy has changed in a few years from the stage of theoretical considerations to that of clinical applications. The first protocol applied to man was initiated in the USA in September 1990 on a patient who was genetically immunodeficient as a result of a mutation affecting the gene encoding adenine deaminase (ADA). The relative success of this first experiment encouraged the development of this technology for various genetic and acquired diseases. The large majority of the current protocols employ vectors to carry the therapeutic gene to the cells to be treated. Numerous viral or synthetic vectors have been developed during these last years. Their structure, organization and biology are described in the literature available to a person skilled in the art.

Adenoviruses have been detected in many animal species, are nonintegrative and not very pathogenic. They are able to infect a variety of cell types, dividing as well as quiescient cells. They have a natural tropism for airway epithelia. In addition, they have been used as live enteric vaccines for many years with an excellent safety profile. Finally, they can be easily grown and purified in large quantities. These features have made adenoviruses particularly appropriate for use as gene therapy vectors for therapeutic and vaccine purposes. Their genome consists of a linear double-standed DNA molecule of approximately 36 kb carrying more than about thirty genes necessary to complete the viral cycle. The early genes are divided into 4 regions dispersed in the adenoviral genome (E1 to E4) which contain 6 transcription units directed by their own promoters. The E1, E2 and E4 regions are essential for viral replication whereas the E3 region, which is believed to modulate the anti-viral host immune response, is dispensable for viral growth in vitro. The late genes (L1 to L5) encode in their majority the structural proteins constituting the viral capsid. They overlap at least in part with the early transcription units and are transcribed from a unique promoter (MLP for Major Late Promoter). In addition, the adenoviral genome carries at both extremities cis-acting regions essential for DNA replication. These are the 5' and 3' ITR (Inverted Terminal Repeat) and a packaging sequence following 5' ITR.

The E4 region is believed to be involved in viral DNA replication, late mRNA synthesis, viral assembly and the shut off of host protein synthesis. It is a complex transcription unit which encodes a variety of polypeptides. Those encoded by the open reading frames (ORFs) 6 and 7 are assumed to compete with the cellular RB protein for the binding to the E2F transcription factor, confering a function of transactivators. The expression product of ORF4 is able to bind and regulate the cellular phosphatase 2A to modulate the activity of viral (E1A) and cellular transcription factors. The polypeptides encoded by ORFs 3 and 6 are essential to viral growth because of their capability to maturate the primary 28 kb transcript derived from the adenoviral genome or its export into the cytoplasm. Their absence might be complemented in trans to allow the viral growth. In addition, the ORF6 polypeptide interacts with the E1B encoded 55K polypeptide to form a complex that facilitates the cytoplasmic accumulation of late messengers at the expense of cellular mRNA.

The adenoviral vectors presently used in gene therapy protocols lack most of the E1 region in order to avoid their dissemination in the environment and the host body. Additional deletions in the E3 region allow to increase the cloning capacity. The gene of interest is introduced into the viral DNA in place of a deleted region. The feasibility of gene transfer using these vectors designated "first generation" has been demonstrated in a number of cases. However, the question of their safety is still under evaluation. Indeed, the probability to generate replication-competent viruses during their propagation in conventional complementing cell lines, is not negligible. Furthermore, the potential immunogenicity of viral proteins still expressed by the viral backbone may reduce the persistence of transduced cells as well as the long term expression of the recombinant transgene and may be associated with inflammatory events.

These major drawbacks have led to the construction of vectors of second generation that retain the cis regions necessary for viral replication (ITRs and packaging sequences) and contain substantial genetic modifications aimed to abolish the residual synthesis of the viral antigens which is postulated to be responsible for the stimulation of inflammatory responses (see for example the international application WO94/28152 or U.S. Pat. No. 5,670,488 which discloses adenoviral vectors partially deleted of E4 sequences with the exception of ORF3 or ORF6/7 that do not need E4 complementation). A minimal vector deficient for the whole adenoviral functions can also be considered.

The persistence of transgene expression is a prerequisite before envisaging the general use of adenoviral vectors in human gene therapy protocols, in particular in view of treatment of chronic and genetic diseases. However, deletion of the E4 region has been recently shown to alter transgene expression conducted by a heterologous promoter (i.e. CMV promoter, RSV LTR). Coinfection studies indicated that E4 products could be supplied in trans to restore stable transgene expression (Armentano et al., J. Virol. 71 (1997) 2408–2416; Brough et al., J. Virol. 71 (1997), 9206–9213).

Thus, the technical problem underlying the present invention is the provision of expression vectors which do not show the instability of transgene expression as observed in E4-deleted adenovirus vectors and of means which allow to obtain long term expression of a transgene in cells.

This problem is solved by the provision of the embodiments characterized in the claims.

Accordingly, the present invention relates to a recombinant adenoviral vector derived from an adenovirus genome in which at least all or part of the E1 region is deleted or non-functional and a part of the E4 region has been deleted and which comprises a gene of interest operably linked to regulatory elements, wherein said adenoviral vector retains sufficient E4 sequences to improve expression and/or persistence of expression of said gene of interest in a host cell or organism. Preferably, the retained E4 sequences consist of:

(i) ORF3 and ORF6+ORF7;

(ii) ORF3 and ORF7;

(iii) ORF3 and ORF6;

(iv) ORF3 and ORF6/7;

(v) ORF3 and ORF4; or (vi) ORFs 1, 2, 3 and 4.

It was surprisingly found that impaired transgene expression in E4-deleted adenoviral vectors could be fully restored by the presence and expression of certain E4 ORFs, in particular of the above-mentioned E4 ORFs.

Although the E4 region may vary between the different adenovirus strains, it can be identified on the basis of nucleotide sequences available in different sources (publications or data bank) or by homology with the well characterized Ad5 E4 region. As an indication, the E4 region is located at the right end of the adenoviral genome, with the E4 promoter being localized 5' to 3' ITR. Transcription occurs from right to left with regards to the adenoviral map. The E4 region reveals 7 open reading frames of which 6 contain an AUG start codon (ORFs 1, 2, 3, 4, 6 and 7) and codes for at least 6 polypeptides (the ORF7 encoded protein has not yet been identified) which can be identified by sequence analysis. mRNA mapping studies have also identified two new ORFs created by mRNA splicing events, i.e. ORF3/4 and ORF6/7. In particular, in the Ad5 genome ORF6 extends from nt 34074 to 33192, ORF7 extends from nt 33111 to 32913 and ORF6/7 extends from nt 34074 to 33901 (splice donor) and 33189 (splice acceptor) to 32913 (see e.g. Cutt et al., J. Virol. 61 (1987), 543–552; Freyer et al., Nucl. Acids Res. 12 (1984), 3503–3519; Virtanen et al., J. Virol. 51 (1984), 822–831). Thus, a recombinant adenoviral vector according to the invention may, inter alia, retain the ORF6, the ORF7 and/or the ORF6/7. A construct retaining ORF6, ORF7 and ORF6/7 contains both ORF6 and ORF7 which can lead to produce the corresponding mRNAs and the splice product ORF6/7. Such a sequence is called ORF6+7 in the scope of the present invention. Furthermore, the recombinant adenoviral vector according to the present invention can also comprise ORF3 and ORF4, which includes the combinations ORF3 and ORF3/4, ORF3/4 and ORF4, ORF3 and ORF4 or just ORF3/4. The person skilled in the art is able to modify the precited E4 region of an adenoviral genome by conventional molecular biology techniques in order to obtain an E4 region which retains the above-mentioned ORFs and lacks the remaining sequences. In particular, it is well within the reach of the person skilled in the art to delete from an adenoviral E4 region a specific portion of DNA, e.g. by appropriate restriction or endonuclease digest and religation. Another possibility is to isolate the retained E4 sequences by PCR.

It is possible for the person skilled in the art to determine those ORFs present in the E4 region which exert a positive effect on transgene expression, e.g. by deleting these ORFs from the E4 region and determining whether they affect transgene expression. Furthermore, it is possible to test the effect of an E4 ORF by providing it in cis or trans to a E4 deleted vector carrying a transgene and determining its effect on transgene expression. Such methods are provided in the examples. The E4 ORF(s) retained in the adenoviral vector is (are) capable alone or in combination, directly or by means of other cellular or viral factors to improve the expression of a gene of interest inserted into the adenoviral vector. This positive effect on transgene expression may be exerted at different levels: transcription, elongation, transport, stability of the transgene mRNA or alternatively translation. The improvement is determined by evaluation of the transgene expression product or persistence of its expression in in vivo or in vitro experiments.

The adenoviral vectors according to the invention moreover may show a reduced hepatotoxicity in comparison to vectors comprising the complete E4 region.

Preferably, the recombinant adenoviral vectors retains the entire coding sequences of one or more of the above-mentioned E4 ORF(s) extending from the initiator ATG to the stop codon. However, it is also feasible to employ a functional variant having promoter regulation capacities. Such a variant may be obtained by mutation or truncation of the native ORF sequences. To illustrate this embodiment, one may refer to an E4 ORF6 variant deleted of the sequence comprised between the first and the second ATG codon. More preferably, the E4 ORFs retained in the adenoviral vector comprise regulatory elements allowing their expression, more preferably their natural regulatory elements, in particular the E4 promoter. Alternatively, they can also be operably linked to a heterologous promoter. In order to stabilize expression of the E4 ORFs, it may be advantageous that the E4 ORF(s) retains or comprises splicing sequences. They may be homologous (to the E4 sequences) or heterologous (i.e., derived from any eukaryotic gene or of synthetic origin). In principle all splicing sequences described in the prior art are suitable, e.g. those of the genes encoding $\alpha$ or $\beta$ globin, apolipoprotein, immunoglobulin, factor IX, factor VIII, CFTR or of the pCI vector (Promega). The E4 ORFs retained in the adenoviral vector according to the invention may be those naturally occurring in such a vector. In particular, they may remain at their natural location. However, it is also possible that the vector is constructed by deleting all E4 sequences, in particular all E4 ORFs, and inserting certain E4 ORFs from the same or other adenovirus backbones in the adenoviral vector at a location where the E4 region normally resides or at a different location, e.g. in place of the deleted E1 or E3 region. The ORFs may be oriented in sense or antisense orientation with respect to the direction of transcription of the wild-type E4 region.

The adenoviral vector according to the invention is an adenoviral vector in which at least all or part of the E1 region is deleted or non-functional. Such a vector can be derived from an adenovirus genome in which at least all or part of the E1 region is deleted. It can be obtained from a parent adenovirus whose genome has been modified. The modifications may be diverse (deletion, mutation and/or addition of one or more nucleotides) and concern any viral sequence. In addition, they may be localized in the coding sequences of the viral genome or outside of these sequences, for example in the regulatory elements such as promoters. As a guide, some viral sequences may be deleted, rendered non functional or replaced by heterologous nucleotide sequences and, in particular gene(s) whose expression is sought in a host cell (one or more gene of interest).

Preferably, the vector according to the invention is defective for E1 functions by total or partial deletion of the respective region. The deletion encompasses at least E1a sequences and may extend in the E1b transcription unit. Preferably the E1b sequences overlapping with pIX gene are not deleted. Such E1 deletions are included in prior art vectors published in the literature.

It goes without saying that the adenoviral backbone of the vector according to the invention may comprise additional modifications, such as deletions, insertions or mutations in one or more viral genes. According to an advantageous embodiment, it is derived from an adenovirus genome in which one or more viral genes of the E2 and/or L1–L5 regions is non-functional. The non functionality may be obtained by a partial or complete deletion or by mutation of one or more of the cited regions. As an example, one may refer to the thermosensible mutation located on the DBP (DNA Binding Protein) encoding gene of the E2a region (Ensinger et al., J. Virol. 10 (1972), 328–339). A defective adenoviral vector deficient in all early and late regions may also be envisaged.

In a further preferred embodiment the vector is deleted of all or part of the E3 region. In this context, it might be interesting to retain the E3 sequences coding for the polypeptides allowing to escape the host immune system, in particular those coding for gpl9k glycoprotein (Gooding et al., Critical Review of Immunology 10 (1990), 53–71).

The adenoviral vector according to the present invention may be derived from a human or animal adenovirus genome, in particular of canine, avian, bovine, murine, ovine, feline, porcine or simian origin or alternatively from a hybrid thereof Any serotype can be employed, in particular the murine adenovirus Mav1 (Beard et al., Virology 175 (1990), 81–90), the canine CAV-1 or CAV-2 (Spibey et Cavanagh, J. Gen. Virol. 70 (1989), 165–172; Linne, Virus Research 23 (1992), 119–133; Shibata et al., Virol. 172 (1989), 460–467; Jouvenne et al., Gene 60 (1987), 21–28), avian DAV (Zakharchuk et al., Arch. Virol. 128 (1993), 171–176) or the bovine BAV3 (Mittal et al., J. Gen. Virol. 76 (1995), 93–102). However, the human adenoviruses of C sub-group are preferred and especially adenoviruses 2 (Ad2) and 5 (Ad5). Generally speaking, the cited viruses are available in collections such as ATCC and have been the subject of numerous publications describing their sequence, organization and biology, allowing the artisan to practice them. For example, the sequence of the human adenovirus type 5 is disclosed in the Genebank data base under the reference M 73260 and is incorporated by reference in its entirety.

As mentioned before, it was found that certain ORFs of the E4 region are capable of regulating positively the expression of a gene of interest inserted in an adenoviral vector. The term "gene" refers to a nucleic acid (DNA, RNA or other polynucleotide derivatives) which can be of any origin (prokaryote, eukaryote, viral . . . ). The gene of interest can code, e.g., for an antisense RNA, a ribozyme or a messenger (mRNA) that will be translated into a protein of interest. It includes genomic DNA, cDNA or mixed types (minigene). It may code for a mature polypeptide, a precursor (i.e. precursor intended to be secreted and comprising a signal sequence, a precursor intended to be maturated by proteolytic cleavage . . . ), a fragment of a protein (truncated protein), a chimeric polypeptide originating from the fusion of diverse sequences or a mutated polypeptide displaying improved and/or modified biological properties. The gene may be isolated from any organism or cell by the conventional techniques of molecular biology (PCR, cloning with appropriate probes, chemical synthesis) and if needed its sequence may be modified by mutagenesis, PCR or any other protocol.

The following genes of interest are of particular interest. They may code for a cytokine ($\alpha$, $\beta$ or $\gamma$ interferon, interleukine (IL), in particular IL-2, IL-6, IL-10 or IL-12, a tumor necrosis factor (TNF), a colony stimulating factor GM-CSF, C-CSF, M-CSF . . . ), a cell or nuclear receptor, a receptor ligand (fas ligand), a coagulation factor (FVIII, FIX . . . ), a growth factor (FGF stating for Fibroblast Growth Factor, VEGF stating for Vascular Endothelial Growth Factor), an enzyme (urease, renin, thrombin, metalloproteinase, nitric oxide synthase NOS, SOD, catalase . . . ), an enzyme inhibitor ($\alpha$1-antitrypsine, antithrombine III, viral protease inhibitor, PAI-1 which stands for plasminogen activator inhibitor), the CFTR protein, insulin, dystrophin, a MHC antigen (Major Histocompatibility Complex) of class I or II or a polypeptide that can modulate/regulate expression of correponding genes, a polypeptide capable of inhibiting a bacterial, parasitic or viral infection or its development (antigenic polypeptides, antigenic epitopes, transdominant variants inhibiting the action of a native protein by competition . . . .), an apoptosis inducer or inhibitor (Bax, Bc2, Bcl X . . . ), a cytostatic agent (p21, p 16, Rb . . . ), an apolipoprotein (ApoAI, ApoAIV, ApoE . . . ), an angiogenesis inhibitor (angiostatin, endostatin . . . ), an oxygen radical scaveyer, a polypeptide having an anti-tumor effect, an antibody, a toxin, an immunotoxin and a marker ($\beta$-galactosidase, luciferase . . . ) or any other genes of interest that are recognized in the art as being useful for the treatment or prevention of a clinical condition.

For example, in view of treating an hereditary dysfunction, one may use a functional copy of a defective gene, for example a gene encoding factor VIII ou IX in the context of haemophilia A or B, dystrophin (or minidystrophin) in the context of myopathies, insulin in the context of diabetes, CFTR (Cystic Fibrosis Transmembrane Conductance Regulator) in the context of cystic fibrosis. Suitable genes of interest to delay or inhibit tumor or cancer progression, include but are not limited to those encoding an antisense RNA, a ribozyme, a cytotoxic product such as thymidine kinase of herpes-1 simplex virus (TK-HSV-1), ricin, a bacterial toxin, the expression product of yeast genes FCY1 and/or FUR1 having UPRTase (Uracile Phosphoribosyl Transferase) and CDase (Cytosine Desaminase) activities, an antibody, a polypeptide inhibiting cellular division or transduction signals, a tumor suppressor gene (p53, Rb, p73. . . ), a polypeptide activating host immune system, a tumor-associated antigen (MUC-1, BRCA-1, an HPV early or late antigen (E6, E7, L1, L2. . . ) . . .), optionally in combination with a cytokine gene. Finally, in the context of anti-HIV therapy, one may use a gene encoding an immunoprotective polypeptide, an antigenic epitope, an antibody (2F5; Buchacher et al., Vaccines 92 (1992), 191–195), the extracellular domain of CD4 (sCD4; Traunecker et al., Nature 331 (1988), 84–86), an immunoadhesine (i.e. CD4-IgG hybrid, CD4-2F5 fusion; Capon et al., Nature 337 (1989), 525–531; Byrn et al., Nature 344 (1990), 667–670), an immunotoxin (i.e. resulting from fusion between angiogenine and 2F5 or CD4-2F5; Kurachi et al., Biochemistry 24 (1985), 5494–5499), a trans-dominant variant (EP 0614980, W095/16780), a cytotoxic product (see above) or IFN$\alpha$ or $\beta$.

In addition, a gene of interest may also comprise a selection gene allowing the selection of transfected and transduced cells. Such genes include but are not limited to the neo gene (encoding neomycin phosphotransferase) confering resistance to G418, dhfr (Dihydrofolate Reductase), CAT (Chloramphenicol Acetyl transferase), pac (Puromycine Acetyl-Transferase) and gpt (Xanthine Guanine Phosphoribosyl Transferase). Selection genes are known in the art.

The gene of interest may be engineered as a functional expression cassette, including a suitable promoter. It may be obtained from any viral, bacterial or eukaryotic gene (even from the gene of interest), be constitutive or regulable. Cptionally, it may be modified in order to improve its transcriptional activity, delete negative sequences, modify its regulation, introduce appropriate restriction sites etc. Suitable promoters include but are not limited to the followings: adenoviral E1a, MLP, PGK (Phospho Glycerate Kinase), MT (metallothioneine; Mc Ivor et al., Mol. Cell Biol. 7 (1987), 838–848), α-1 antitrypsin, CFTR, surfactant, immunoglobulin, β-actin (Tabin et al., Mol. Cell Biol. 2 (1982), 426–436), SRα (Takebe et al., Mol. Cell. Biol. 8 (1988), 466–472), early SV40 (Simian Virus), RSV (Rous Sarcoma Virus) LTR, TK-HSV-1, SM22 (WO 97/38974), Desmin (WO 96/26284) and early CMV (Cytomegalovinis). Alternatively, the promoter may be stimulated in tumor or cancerous cells. As an example, one may employ the promoters isolated from MUC-1 gene overexpressed in breast and prostate cancers (Chen et al., J. Clin. Invest. 96 (1995), 2775–2782), CEA (Carcinoma Embryonic Antigen) overexpressed in colon cancers (Schrewe et al., Mol. Cell. Biol. 10 (1990), 2738–2748), tyrosinose overexpressed in melanomas (Vile et al., Cancer Res. 53 (1993), 3860–3864), ERB-2 overexpressed in breast and pancreas cancers (Harris et al., Gene Therapy 1 (1994), 170–175) and α-foetoprotein overexpressed in liver cancers (Kanai et al., Cancer Res. 57 (1997), 461–465). The early CMV promoter is preferred in the context of the invention.

The regulatory elements may further include additional elements, such as intron(s), secretion signal, nuclear localization signal, IRES, poly A transcription termination sequences, tripartite leader sequence and replication origins.

The adenoviral vector according to the present invention may comprise one or more gene(s) of interest. The different genes may be included in the same cassette or in different cassettes thus controled by separate regulatory elements. The cassettes may be inserted into various sites within the vector in the same or opposite directions.

In another aspect the present invention also relates to the use of a polynucleotide comprising one or more open reading frames (ORFs) of the E4 region of an adenovirus selected from the group consisting of ORF1, ORF2, ORF3, ORF4, ORF3/4, ORF6/7, ORF6 and ORF7, either alone or in combination, to improve the expression and/or persistence of expression of a gene of interest which is contained in an expression vector and is operably linked to regulatory elements.

The finding that the presence of certain ORFs of the adenoviral E4 region is advantageous for the stable expression of transgenes is also of importance for obtaining stable expression of transgenes in expression vectors others than adenoviral vectors. Thus, the above-mentioned ORFs of an adenoviral E4 region can generally be used to achieve stable expression of transgenes in expression systems. In this regard, it is possible to achieve improved expression, i.e. expression at all or stable long term expression, of a transgene either by providing the ORFs in cis or in trans.

As indicated above in connection with the adenoviral vectors according to the invention, the E4 region may vary between the different adenovirus strains. However, it is well within the skill of the person skilled in the art to identify the E4 region of an adenovirus as well as the ORFs contained in it. Thus, it is possible for the person skilled in the art to isolate the above-cited ORFs from an adenoviral genome in order to use them according to the invention.

The E4 ORF(s) used in the scope of the present invention may be from any adenoviral origin (animal or human). Preferably they are derived from a human adenovirus of sub-group C, particularly preferred from Ad2 or Ad5.

The E4 ORF(s) is (are) capable alone or in combination, directly or by means of other cellular or viral factors to improve the expression of a gene of interest inserted into an expression vector. This positive effect on transgene expression may be exerted at different levels: transcription, elongation, transport, stability of the transgene mRNA or alternatively translation. The improvement is determined by evaluation of the transgene expression product or persistence of its expression in in vivo or in vitro experiments. One way to proceed is to inject a vector carrying said E4 ORF(s) together with an expression cassette of a gene whose product is easily detectable (LacZ, luciferase, α1-antitrypsin, factor IX, CFTR . . . ) and to determine the level of transgene product over time compared to a control that is devoided of E4 adenoviral sequences. The improvement can be seen in terms of the amount of transgene product (at least by a factor 2) or in terms of persistence of the expression (stability over a longer period of time).

In a preferred embodiment of the use according to the invention, a polynucleotide is used which comprises (i) ORFs 1, 2, 3 and 4;

(ii) ORFs3,6+7;

(iii) ORFs 3 and 7;

(iv) ORFs 3 and 6;

(v) ORF 3 and ORF 6/7;

(vi) ORFs 3 and 4; or (vii) ORF 3/4 of an adenoviral E4 region.

Preferably, such an ORF comprises the complete coding sequence, i.e. from the initiator ATG to the stop codon. However, it is also possible to employ a functional variant of such an ORF, e.g. variants obtained by deletion, mutation or truncation which still encode a functional polypeptide. Variants include in particular such ORFs which share a high degree of homology to the native equivalent, in particular at least 70% sequence identity, more preferably at least 80% and even more preferred at least 90%. Particularly preferred is absolute identity.

The polynucleotide used in the present invention is operably linked to regulatory elements to allow its expression in a host cell or organism. Such elements include a promoter that may be isolated from any gene of eukaryotic or viral origin. When the polynucleotide comprises several E4 ORFs, these may be expressed from a unique promoter or independent ones. In this case, the different E4 cassettes may be in the same or opposite direction and in the same and different locations within one or more vector(s). However, the use of a unique promoter to drive transcription of the selected E4 sequences is preferred. A first possibility is to place them under the control of the homologous E4 promoter. Another alternative is to use a heterologous promoter. Such a heterologous promoter is preferably constitutive and may be chosen among those cited hereinafter. The person skilled in the art is capable to link said polynucleotide to an appropriate promoter in an operative way. In order to stabilize expression, it may be advantageous that the E4 ORF(s) retains or comprises splicing sequences. They may be homologous (derived from E4 sequences) or heterologous (derived from any eukaryotic gene or from synthetic origin). The large variety of splicing sequences described in the state of the art are suitable in the context of the invention. One may cite more particularly those isolated from genes encoding α or β globin, apolipoprotein, immunoglobulin, factor IX, factor VIII, CFTR and from the pCI vector (Promega).

Advantageously, the polynucleotide sequence is inserted in an expression vector. In the context of the present invention, it can be a plasmid, a synthetic or a viral vector.

Plasmid denotes an extrachromosomic circular DNA capable of autonomous replication in a given cell. The choice of the plasmids is very large. It is preferably designed for amplification in bacteria and expression in eukaryotic host cell. Such plasmids can be purchased from a variety of manufactors. Suitable plasmids include but are not limited to those derived from pBR322 (Gibco BRL), pUC (Gibco BRL), pBluescript (Stratagene), pREP4, pCEP4 (Invitrogene), pCI (Promega) and p Poly (Lathe et al., Gene 57 (1987), 193–201). It is also possible to engineer such a plasmid by molecular biology techniques (Sambrook et al., Laboratory Manual, Cold Spring Harbor Laboratory Press, Cold Spring Harbor (1989), N.Y.). A plasmid may also comprise a selection gene in order to select or identify the transfected cells (by complementation of a cell auxotrophy, antibiotic resistance), stabilizing elements (i.e. cer sequence; Summers and Sherrat, Cell 36 (1984), 1097–1103) or integrative elements (LTR viral sequences).

An expression vector may also be from viral origin and may be derived from a variety of viruses, such as herpes viruses, cytomegaloviruses, AAV (adeno-associated virus), poxviruses (canarypox, fowlpox, vaccinia virus, MVA) and retroviruses.

In a preferred embodiment the polynucleotide and gene of interest are inserted into the same expression vector. They may be inserted in the same location (i.e. in place of the deleted E1 sequences in an E1⁻ adenoviral vector) or at different locations (e.g., the gene of interest in place of the deleted E1 sequences and the polynucleotide in place of the native E4 region). The use of two independant expression vectors each carrying said polynucleotide and gene of interest is also feasible. In this case, both vectors may be introduced in the host cell together (co-transfection or co-infection) or separately.

In a particularly preferred embodiment the vector into which the polynucleotide comprising the E4 ORFs are inserted, is an adenoviral vector, preferably one from which the E4 region has been deleted.

With respect to the nature and structure of the adenoviral vector, the location of the inserted E4 ORFs, the nature of the gene of interest and the regulatory regions, the same applies as already set forth in connection with the adenoviral vectors according to the invention.

Moreover, the present invention relates to a non-adenoviral vector comprising a gene of interest operably linked to regulatory elements and comprising one or more open reading frames (ORF(s)) of the E4 region of an adenovirus selected from the group consisting of ORF1, ORF2, ORF3, ORF4, ORF3/4, ORF6/7, ORF6 and ORF7 taken individually or in combination and operably linked to regulatory elements.

With respect to the combinations and characterisitics of the ORFs and the nature of the gene of interest the same applies as set forth above for the use of a polynucleotide according to the invention.

The present invention also relates to an infectious viral particle comprising an adenoviral vector according to the invention or an expression vector comprising E4 ORFs as described in connection with the use according to the invention. It may be prepared according to any conventional technique in the field of the art. When an adenoviral vector is considered, one may proceed by cotransfection of suitable adenoviral fragments in a cell line such as 293 line (as described in Graham and Prevect, Methods in Molecular Biology, Vol 7 (1991), Gene Transfer and Expression Protocols; Ed E. J. Murray, The Human Press Inc, Clinton, N.J.). It is also possible to reconstitute the vector in *Escherichia coli* by ligation or homologous recombination (as described in WO96/17070) before transfecting the cell line. Furthermore, the virions may be amplified by passage in a permissive cell in order to generate a high titer viral stock that may be used in the preparation of clinical lots. It may be propagated in a complementation cell line, which supplies in trans the deleted/mutated viral functions. Line 293, established from human embryonic kidney cells (Graham et al., J. Gen. Virol. 36 (1977), 59–72) is commonly used to complement the E1 function. Other cell lines have been engineered to complement doubly defective vectors (E1° E4° or E1° E2°), such as those described in Yeh et al. (J. Virol. 70 (1996), 559–565), Krougliak and Graham (Human Gene Therapy 6 (1995), 1575–1586), Wang et al. (Gene Therapy 2 (1995), 775–783), Lusky et al. (J. Virol. 72 (1998), 2022–2033) and in the international applications WO94/28152 and WO97/04119. Alternatively, it is also possible to also use a helper virus supplying in trans at least a part of the viral deficiencies.

The invention also relates to a method for preparing an infectious viral particle according to the invention, according to which:

(i) the adenoviral vector of the invention or the expression vector comprising E4 ORFs as described in connection with use according to the the present invention is introduced into a complementation cell capable of complementing in trans said vector, to obtain a transfected complementation cell;

(ii) said transfected complementation cell is cultured under suitable conditions to permit the production of said infectious viral particle; and (iii) said infectious viral particle is recovered from the cell culture.

The vector can be introduced into the cell line by any one of a variety of methods known in the art. One may proceed by transfection of the vector or fragments thereof, by lipofection, electroporation and infection. The infectious viral particles may be recovered from the culture supernatant but also from the cells which can be lysed, for example, by a series of thawing/freezing cycles. Optionally, the virions may be amplified and purified according to standard techniques (chromatography, ultracentrifugation, for example in a cesium chloride gradient . . . ).

Furthermore, the present invention relates to a host cell comprising an adenoviral vector of the invention or a polynucleotide and an expression vector as defined in connection with the use of the invention or infected by an infectious viral particle of the invention. Preferably, such a cell is from mammalian origin and, in particular from human origin. The vector may be inserted into the cellular genome or not (episome). Suitable cells include but are not limited to primary or tumoral cells, from haematopoietic (totipotent stem cell, leucocyte, lymphocyte, monocyte, macrophage . . . ), muscular (satellite cell, myocyte, myoblaste, smooth muscle cells . . . ), cardiac, lung, tracheal, liver, vascular, epithelial, fibroblastic or endothelial origin.

The present invention also relates to a composition, preferably a pharmaceutical composition, comprising as an agent an adenoviral vector according to the invention, a polynucleotide and an expression vector as described in connection with the use of the invention, a host cell or an infectious viral particle according to the invention or prepared according to the process of the invention. The composition of the invention is intended especially for the preventive or curative treatment of disorders such as genetic diseases (haemophilia, diabete, cystic fibrosis, Duchenne or Becker myopathies, auto-immune diseases) or acquired disorders (cancers, tumors, cardiovascular diseases, viral diseases such as AIDS or hepatitis B or C . . . ).

The composition according to the invention may be manufactured in a conventional manner for local, general or oral administration. Aerosol, intillation or injection may be envisaged. Suitable routes of administration include intragastric, subcutaneous, intracardiac, intramuscular, intravenous, intraarterial, intraperitoneal, intratumoral, intranasal, intrapulmonary or endotracheal routes. The administration may take place in a single dose or a dose repeated one or several times after a certain time interval. The appropriate administration route and dosage vary in accordance with various parameters, for example, with the individual, the disorder to be treated or with the gene of interest to be transferred. The viral particles according to the invention may be formulated in the form of doses of between $10^4$ and $10^{14}$ iu(infectious unit), advantageously $10^5$ and $10^{13}$ iu and preferably $10^6$ and $10^{12}$ iu. The titer may be determined by conventional techniques (see for example Lusky et al., 1998, supra). Doses based on vector may comprise between 0.01 and 100 mg of DNA, advantageously 0.05 and 10 mg and preferably 0.5 and 5 mg. In addition, the agent of the composition may be combined with a vehicle which is acceptable from a pharmaceutical standpoint. The formulation may also include a diluent, an adjuvant or an excipient. It may be presented as a liquid directly injectable or as a dry powder (lyophylized . . . etc) that can be reconstituted before use.

In addition, the vector, host cell and viral particles according to the present invention can optionally be combined with one or more substances improving gene transfer efficiency or stability. Such substances are well known in the ,art (see for example Felgner et al. (Proc. West. Pharinacol. Soc. 32 (1987), 115–121); Hodgson and Solaiman (Nature Biotechnology 14 (1996), 339–342); Remy et al. (Bioconjugate Chemistry 5 (1994), 647–654)) and include in particular polymers, cationic lipids, liposomes, nuclear proteins and neutral lipids. They may also be used in combination (i.e. cationic and neutral lipids).

Moreover, the present invention relates to the use of an adenoviral vector according to the invention, a polynucleotide and an expression vector, as described in connection with the use according to the invention, a viral particle or a host cell according to the invention for the preparation of a drug intended for gene transfer into a host cell or organism and preferably for the treatment of human or animal body by gene therapy or immunotherapy. According to a first possibility, the drug may be administered directly in vivo (for example by intravenous injection, in an accessible tumor, in the lungs by aerosol . . . ). It is also possible to adopt the ex vivo approach which consists in removing cells from the patient (bone marrow stem cells, peripheral blood lymphocytes, muscle cells . . . ), transfecting or infecting them in vitro according to standard protocols and readministering them to the patient.

In a preferred embodiment of said use of the present invention the retained E4 sequences in said adenoviral vector are:

(i) ORFs 3 and 4;
(ii) ORF 3/4;
(iii) ORFs 3 and 6+7;
(iv) ORFs 3 and 6;
(v) ORFs 3 and 7; or
(vi) ORF 3 and 6/7.

Preferably, the corresponding pharmaceutical compositions are for gene transfer into lung tissue.

In another preferred embodiment of said use of the present invention the retained E4 sequences in said adnoviral vector are:

(i) ORF 3;
(ii) ORFs 3 and 4;
(iii) ORF 3/4;
(iv) ORFs 3 and 6+7;
(v) ORFs 3 and 6;
(vi) ORFs 3 and 7; or
(vii) ORFs 3 and 6/7.

Preferably, the corresponding pharmaceutical compositions are for gene transfer into liver tissue.

The adenoviral vectors mentioned in context with said preferred embodiments of the use of the present invention display a reduced toxicity and/or provoke a reduced inflammatory response by the host cell or host organism. This will be illustrated by the examples which will follow below.

The present invention also relates to a method of treatment according to which a therapeutically effective amount of an adenoviral vector according to the invention, a polynucleotide and an expression vector as described in connection with the use according to the invention, a viral particle or a host cell according to the invention is administered to a patient in need of such a treatment.

Finally, the invention also provides a product comprising:

(i) an expression vector comprising a gene of interest operably linked to regulatory elements; and
(ii) a polynucleotide as defined above in connection with the use according to the invention;

as a combination product for a simultaneous or separate use.

According to this embodiment, the expression vector is conventional and may be derived from a plasmid or a virus. The term vector encompasses the free genome (DNA) or the genome packaged in a viral capsid (virion). As indicated before, the polynucleotide may also be inserted in such a vector.

Materials and Methods

The constructions described below are carried out according to the general techniques of genetic engineering and molecular cloning detailed in Sambrook et al. (1989, Laboratory Manual, Cold Spring Harbor, Laboratory Press, Cold Spring Harbor, N.Y., or more recent editions) or according to the manufacture's recommendations when a commercial kit is used. Homologous recombination steps preferentially employ the strain E. Coli BJ 5183 (Hanahan, J. Mol. Biol. 166 (1983), 557–580) and are performed as described in Chartier et al. (J. Virol. 70 (1996), 4805–4810). Regarding the repair of restriction sites, the technique employed consists of filling in the 5' protuding ends using the large fragment of E. coli DNA polymerase I (Klenow). The adenoviral genome fragments employed in the different constructions described below are indicated precisely according to their positions in the nucleotide sequence of the Ad5 genome as disclosed in the Genebank databank under the reference M73260.

Regarding the cell biology, the cells are transfected or transduced according to the standard techniques well known to a person skilled in the art. The calcium phosphate technique may be mentioned but any other protocol may also be employed. The culture conditions are, for their part, conventional. Line 293 (Graham et al, 1977, supra ; ATCC CRL-1573) results from the integration in its chromosomes of the 5' end of the Ad5 genome. Line TG5606 (described in Lusky et al. (1998), supra) is derived from line 293 stably transfected by the plasmid pTG5606 carrying the Ad5 E4 ORF6+7 (i.e. a sequence containing both ORF6 and ORF7 susceptible to produce the corresponding polynucleotides and the splice product ORF6/7) sequences and the pac selectable gene. A549 is available at ATCC (CCL-125). Other cell lines may be used as well.

Virus generation, viral growth and titration. For the generation of viruses, the viral genomes were released from the respective recombinant plasmids by PacI digestion and transfected into the appropriate complementation cell lines, as described previously (Chartier et al., 1996, J. Virol 70, 4805–4810). Wild type E4 vectors were generated in 293 cells, whereas all E4-modified vectors were generated in TG5606 cells. Virus propagation, purification and titration of infectious units (IU/ml), by indirect DBP inimunofluorescence was exactly as described (Lusky et al, 1998, supra). Viral particle concentration (P/ml) of each vector preparation was calculated using the optical density for measurement of viral DNA content (Mittereder et al., 1996, J. Virol. 70, 7498–7509). Growth of E4-modified vectors in the presence and absence of E4 complementation was assessed in 293 and compared to that in TG5606 cells.

Animal studies. The mice used in this study were 6 to 8 weeks old female immunocompetent C57Bl/6, CBA or immunodeficient C.B17-scid/scid mice (IFFA Credo, L'albresle, France). The vectors containing the CFTR transgene were administered intratracheally (I.T.) or intravenously (IV) at the indicated doses. Animals were sacrificed at the times indicated. Organs were removed, cut into equal pieces and immediately frozen in liquid nitrogen until analysis.

DNA analysis. Total DNA was extracted from tissue culture cells and organs as described (Lusky et al., 1998, supra). Briefly, the cells or tissues were digested overnight with proteinase K solution (1 mg proteinase K in 1% SDS) in DNA lysis buffer (10 mM Tris-HCL pH 7.4, 400 mM NaCl, 2 mM EDTA). The DNA was isolated by phenol-chloroforn extraction followed by ethanol precipitation. DNA (10 μg) was digested with BamHI and analyzed by Southern blot analysis using a $^{32}$P-labeled EcoRI-HindIII restriction fragment purified from Ad5 genomic DNA (nt 27331 to 31993).

RNA analysis. Total RNA was extracted from tissue culture cells and organs as described and as recommended by the supplier. For Northern blot analysis, 10–15 μg of total RNA was subjected to gel electrophoresis and transferred to nitrocellulose filters. CFTR-specific mRNA was detected using a $^{32}$P-labeled BamHI restriction fragment (2540 bp) purified from the CFTR cDNA. Virus specific mRNA was detected using a $^{32}$P-labeled oligonucleotide, specifically hybridizing to the hexon mRNA of the viral L3 messages.

Toxicity studies. Toxicity studies of the different adenoviral constructs were conducted on six weeks-old immunocompetent female mice (C57BL/6, Balb/c, C3H or CBA) purchased from Iffa Credo (L'albresles, France). Mice were housed in specific pathogen-free facilities. Adenoviral vectors were delivered via intravenous (i.v.) administration by tail vein infusion of a volume of 1005 μl. Animals were sacrificed at different time points over a period of at least one month (5, 16 and 30 or 4, 14, 30 and 60 days). Livers were removed and stored in 10% formaldehyde buffer until anatomopathological analysis. Viral particles concentration was calculated using the optical density for measurement of viral DNA content (Mittereder et al., 1996, J. Virol. 70, 7498–7509).

Anatomopathological analysis was performed on 10% formalin-fixed, paraffin-embedded tissues stained with hematoxilin and eosin. Liver damages (dystrophy) and inflammation status (lymphocytic infiltration) were visually estimated.

Liver toxicity was evaluated by analysing transaminases contents from serum samples taken at the time of sacrifice. GOT (glutamic oxalacetic transaminase) and GPT (glutamic pyruvic transaminase) levels were measured by a standard enzymatic method. GOT is representative of aspartate aminotransferase (AST) activity which catalyses the transfer of an amino group between L-aspartate and 2-oxaloglutarate to give L-glutamate and oxaloacetate, the latter reacting with NADH in the presence of malate deshydrogenase. The NADH oxidation rate is evaluated as the reduction of optical absorbance at 340 nm (Cobas Integra) and is directly proportional to AST catalytic activity. GPT is representative of alanine aminotransferase (ALT) activity which catalyses the reaction between L-alanine and 2-oxoglutarate to give L-glutarnate and pyruvate, the latter reacting with NADH in the presence of lactate dehydrogenase. The NADH oxidation rate was evaluated as the reduction of optical absorbance at 340 nm and is directly proportional to ALT catalytic activity.

The following examples serve to illustrate the present invention.

EXAMPLE 1

Construction of E4 Modified Vectors

A series of isogenic AdE1° and AdE1° E4° vectors were generated carrying CMV promoter driven expression cassettes. All vectors have an adenoviral backbone deleted of the essential of E1 sequences (deletion of nt 459 to 3327) and E3 (either a small deletion (S) covering nt 28592 to 30470) or a large (L) one extending from nt 27871 to 30748). Nucleotide numbering throughout the specification is according to Chroboczek et al. (Virology 186 (1992), 280–285) (or ATCC M73260). They all contain the human CFTR cDNA transcribed from the hCMV promoter and terminated by the βglobin poly A signal, inserted in place of E1 region. The following vectors differ by the size of the E4 deletion. But they all use the viral E4 promoter to drive expression of the E4 region or individual E4 ORF(s). They are constructed as infectious plasmids by homologous recombination in E coli as described in Chartier et al. (1997, supra) and Lusky et al. (1998, supra). The viruses are generated in either E1 (293) or E1 and E4 (TG5606) complementation cell lines according to their deficiencies. The vectors carrying the complete E4 region and the E4 ORF6/7 do not need complementation of E4 functions. In addition, in all vectors the endogeneous polyA site is used.

AdTG6421 contains the E4 ORFs 6+7 (i.e., a sequence containing both ORF6 and ORF7 susceptible to produce the corresponding polynucleotides and the splice product ORF6/7). The sequence between BglII (nt 34112) and Avrll (nt 35461) restriction sites have been deleted and the ends were blunted and ligated.

AdTG6447 contains ORFs 1 to 4 and has the ORFs 6 and 7 deleted. This was done by deleting the viral sequences nt 32827 to 33985 between the MunI site (nt32822) and the AccI site (nt 33984). The sites were then blunted and ligated.

AdTG6449 contains the E4 ORFs 3 and 4. It is obtained from AdTG6447 further deleted from ORFs 1 and 2 sequences extending from nt 34799 to 35503 by restriction cutting with PvuII (nt 34796) and Eco47-3 (35501) and religation.

AdTG6477 is derived from AdTG6449 and has the ORF4 inactivated by partial deletion between the TthI (nt34064) and NarI (nt34189) sites. Thus this vector contains the E4 ORF3.

AdTG6487 is derived from AdTG6447 by deletion of the sequences extending from nt 34632 and 35503 between the SspI and Eco47-3 sites. Thus this vector contains the E4 ORF4.

AdTG6490 contains two separate deletions. First ORFs 1 and 2 are deleted of nt 34799 to 35503 between PvuH site (nt 34796) and Eco47-3 (35501). In addition ORF4 is inactivated by deletion of the sequences nt 34069 to 34190 between the TthI (nt 34064) and NarI (nt 34189). Thus this vector contains the ORFs 3, 6+7. It should be noted that E4 ORF6 lacks the first ATG (nt 34074). Since the vector can be amplified in 293 cells in the absence of E4 complementation, one may assume that translation starts at the second ATG (nt 34047) and the resulting product is functional.

AdTG6418 is a positive control that has all the features described above and contains the wild type E4 region (E4+). AdTG5643 is the negative control that contain a large deletion in E4 region (E4°). This E4 deletion is identical to the H2dl808 deletion in Ad2 (Challberg and Ketner, Virology 114 (1981), 196–209) removing most of the E4 coding sequences with the exception of ORF1 (Lusky et al. (1998), supra).

The viral particles were harvested, purified and titered as described in Lusky et al. (1998, supra). AdTG6418 was produced in 293 cells whereas all others were produced in 293-E4 (TG5606) cells. The titration data are given in the following Table 1 which also summarizes the features of the vector backbone.

TABLE 1

| Virus | deletion E3 | E4 region | titer in IU/ml |
|---|---|---|---|
| 6418 | S | wild type (E4+) | $1 \times 10^{11}$ |
| 5643 | S | E4° (ORF1+) | $2 \times 10^{11}$ |
| 6421 | L | ORF 6 + 7 | $2.3 \times 10^{11}$ |
| 6447 | S | ORF 1–4 | $2 \times 10^{11}$ |
| 6449 | S | ORF 3 and 4 | $2.2 \times 10^{11}$ |
| 6477 | S | ORF 3 | $1.3 \times 10^{11}$ |
| 6487 | S | ORF 4 | $1 \times 10^{11}$ |
| 6490 | S | ORF 3, 6 + 7 | $3.8 \times 10^{11}$ |

The result indicate that deletion within E4 region does not impair the viral growth as shown by similar triration as soon as adequate complementation is provided. Moreover, deletion of all E4 ORFs 3, 6 and 7 has a beneficial effect, allowing more infectious viruses to be produced.

Earlier studies had indicated that Ad vectors containing either the E4 ORFs 3, or 6 or 6+7 maintained the ability to propagate in the absence of E4 complementation (Huang and Hearing, 1989, J. Virol. 63, 2605–2615). Therefore, to ascertain the functionality of individual or combinations of E4 ORFs in our vectors, growth of these vectors was monitored in the absence of E4 complementation (293 cells) or in the presence of E4 complementation (TG5606 cells). Consistent with the data by Huang and Hearing, the Vectors containing the E4 ORF 6+7 (AdTG6421) or the E40RFs 3, 6+7 (AdTG6490) were capable of propagating to high yields in 293 cells, similar to the yields obtained with the vector containing the wt E4 region (AdTG6418). In this context, it should be pointed out, that in the vector AdTG6421 translation of the E4 ORF6 and E4 ORF6/7 proteins can start at the first ATG present in the ORF6 translational frame. In contrast, the first ATG of the E4 ORF6 and E4 ORF6/7 proteins in the vector AdTG6490 has been deleted in the course of this vector construction. Thus, translation of the E4 ORFs 6 and 6/7 must use the second ATG (amino acid 10) in the ORF6 translational frame. Since this vector (AdTG6490) can propagate to high levels in 293 cells, these data indicate that the first nine N-terminal amino acids of the E4 ORF 6 and 6/7 proteins are dispensable, at least for viral growth.

The vectors containing E4 ORFs 1–4 (AdTG6447) and the E4 ORFs 3+4 (AdTG6449) were also capable of propagating in the absence of E4 complementation, albeit at reduced levels (100 fold reduced compared to the wt E4 vector). Growth of the vector containing only ORF3 (AdTG6477) was apparent in 293 cells, although the viral yields were reduced approximately 1000 fold, when compared to that of the wt E4 vector. Thus, growth of the vectors AdTG6447, AdTG6449 and adTG6477 confirmed the functionality of the ORF 3 in these constructs. The vectors, containing E4 ORF4 (AdTG6487) or ORF1 (AdTG5643) were unable to propagate in 293 cells as previously reported (Lusky et al, 1998, supra). All vectors, however, were capable of propagating up to high titers in the presence of E4 complementation.

EXAMPLE 2

CFTR Expression

A. Effect of the E4Function on the Activation of CMV Promoter.

E1° (AdTG6418) and E1° E4° (AdTG5643) vectors were used to infect non-complementing human A549 cells in vitro at a moi of 100 IU/cell. Total cellular RNA was extracted from the infected cells at 72 h p.i. and analyzed for the steady state level of CFTR mRNA using a CF specific probe. The results showed strong CFTR expression from the E1° vector. In contrast, CFTR expression could not be detected from the E1° E4° vector. These data indicate that the viral E4 region might influence the transcription from the CMV promoter used to drive CFTR expression. However, strong steady state levels are restored by coinfection with CFTR-less vectors containing the wild type E4 region or the E4 region ORF1–4, which indicates that certain E4 gene products can activate CMV driven transgene expression. Similar results were obtained using the RSV promoter. In the absence of the E4 region, RSV driven transgene expression was shut off and could be restored by the E4 region in trans.

B. Transgene Expression in Immunodeficient Mice.

The AdE1° and E1° E4° vectors were injected intratracheally (IT) into Scid mice (viral dose $1.5 \times 10^9$ IU/animal). For the E1° vector, the persistence of viral genomes and CFTR mRNA was monitored up to 100 days p.i., Viral DNA was detected by Southern blot analysis with a radioactively adenoviral restriction fragment. The signal was then quantitated by densitometry scanning of the autoradiographs (GS-700 Imaging densitometer ; Bio-Rad). Steady state level of CFTR mRNA was evaluated as before.

Although the quantity of AdE1° genomes steadily declined over time to less than 10% of the initial values, surprisingly, initial strong CFTR expression from the CMV promoter, was maintained and induced over a period of 100 days, despite of the clearance of the viral genomes. Thus, with vectors containing the E4 region, viral genomes were actively cleared, but transgene expression remained constant and even appeared to be activated over time.

A similar analysis was carried out for the corresponding AdE1° E4° vector. Clearance of viral genome occured virtually identical to that seen with the E1° vector. WVhile CMV-driven transgene expression at 3 days p.i. was very similar to that seen with the E1° vector, by 14 days p.i. transgene expression from E1°E4° vector was abruptly shut off. Since the persistence and clearance of viral genomes is virtually identical for the E1° and E1°E4° vectors, the expression data indicate that the potential of the CMV expression cassette appeared to be enhanced in the presence of the E4 region.

To explore this issue, E1°E4° CFTR vector was coinjected with a CFTR less vector E1° E4ORF1–4 (AdTG4680). The results show that the presence of the E4 ORF1–4 in trans allowed for strong and stable CFTR transgene expression. In a second experiment, Scid mice injected with the AdE1°E4° CFTR vector were reinjected at day 45 p.i. with AdTG4680, leading to a rescue of CMV driven transgene expression within 14 days. These results indicate that the CMV promoter was not irreversibly silenced.

C. Transgene Expression in Immunocompetent Mice.

Viral genome persistence and CFTR transgene expression was also monitored and compared in immunocompetent mice injected with AdTG6418 (E1°) or AdTG5643 (E1° E4°) containing the CMV-CFTR expression cassette. In C57Bl/6 mice the kinetics of DNA clearance for both types of vectors was very similar, the copy number of viral genomes being reduced to less than 10% of the initial values within 14 days p.i. In CBA mice, the AdE1°E4° vector genome was cleared with similar kinetics. In contrast, the AdE1° vector genome dropped to less than 1% of the initial values by 14 days p.i.

Transgene expression from the AdE1°E4° vector in both C57bl//6 and CBA mice was not stable and undetectable by 14 days p.i. Surprisingly, transgene expression from the AdE1° vector was shut off by 14 d p.i. only in CBA mice. However, in C57Bl/6 mice, CFTR expression from the AdE1° vector was still observed after 120 days p.i. These results support the idea that the C57Bl6mice are somehow tolerant for the transgene. In addition, the maintenance of AdE1°-CFTR transgene expression might also be influenced by the E4 transcriptional activating functions.

D. Functional Dissection of the Viral E4 Region.

To further explore transcriptional activation from the viral E4 region, vectors containing individual E4 ORFs and combinations thereof were evaluated in vitro and in vivo in Scid mice as described before.

After transduction of A549 cells, viral DNA was detected in all samples, indicating that deletions within the E4 region do not alter the in vitro DNA persistence. However, steady state level of CFTR mRNA varied dramatically according to the different samples. As expected, a strong signal was observed with the positive control AdTG6418 (E1°E4+) whereas deletion of the E4 region (AdTG5643) resulted in a complete shut off of the CFTR expression. The presence of ORF3 (AdTG6477), ORF4 (AdTG6487) or ORF6+7 (AdTG6421) partially restored transgene expression. However, the level of CFTR mRNA remained very weak compared to the one obtained with the positive control (wild type E4). The presence of ORFs 3 and 4 (AdTG6449) almost fully restored the activity of the CMV promoter as did the presence of ORFs 1 to 4 (Ad TG6447). However, in the presence of ORFs3, 6+7 (AdTG6490) the activity of the CMV promoter is even improved compared to that of wildtype.

The experiments show that, in the presence of the viral E4 region, transgene expression in the lung (I.T.) was stable up to 100 days. In contrast, deletion of the viral E4 region resulted in a complete shut off of gene expression between 3d and 14 d p.i. In an AdE1°E4° background transgene expression could be activated in trans by the viral E4 ORFs 1–4. Furthermore, in mice containing the AdE1°E4°-CFTR vector transgene expression could be rescued by injection of an AdE1°E40RF1–4 vector 45 d after the initial injection. This result indicates that the CMV promoter was not irreversibly silenced and that E4 gene product(s) positively regulate the CMV promoter. Our data with individual E4 ORF(s) indicate that the transactivation function(s) are maintained in vectors containing the E4 region ORF3 plus ORF4 or ORF3 plus ORF6+7.

E. Tissue-specific Expression.

To monitor the effect of the E4 modifications on the activation and persistence of transgene expression in vivo, without any interference with host immune responses, 1.5× $10^9$ virions of each construct (bearing wtE4, ORFs1–4, ORFs 3 and 4, ORFS 3, 6 and 7, ORF 3 or ORF1 alone) were administered by intratracheal (I.T.) and intravenous (I.V.) injections into immunodeficient Scid mice. Vector persistence and transgene expression were monitored over time (3, 14, 45 and 83 days in the lung tissue and 3, 14 and 30 days in the liver tissue) in the lungs and livers of the infected animals by Southern blot analysis and by CFTR Northern blot analysis respectively.

In the lungs, vector clearance was similar for all vectors and occurred at similar rates, with the exception. of the vectors containing the E4 ORFs 3 (AdTG6477) and the E4 ORFs 3, 6+7 (AdTG6490), which appeared to be more stable over time. All vectors expressed the transgene initially (day 3 p.i.) to high and comparable levels. However, as observed with the doubly deleted vector AdE1°E4°, CFTR expression was shut off between day 3 and 14 p.i. with the vectors containing the E4 ORF3 (AdTG6477), the E4 ORF 4 (AdTG6487) and the E4 ORFs 6+7(AdTG6421). In contrast, CFTR expression persisted, although to different levels, with the vectors containing the E4 ORFs 1–4 (AdTG6447), E4 ORFs 3+4 (AdTG6449) and the vector containing the E4 ORFs 3, 6+7 (AdTG6490) over a period of 83 days (the duration of the experiment). Interestingly, transgene expression obtained with the AdTG6490 vector seemed to persist at constitutively high levels over the time monitored and the steady state levels of CFTR mRNA were even higher than those obtained with the wt E4 vector (AdTG6418). In contrast, transgene expression from the E4 ORF1–4 (AdTG6447) and E4 ORF3,4 (AdTG6449) vectors, while persistent, were not at constitutively high levels. With these vectors transgene expression appeared reduced at day 14 p.i., followed by an induction at day 45, before it reduced again at day 83 p.i.

A similar pattern of CFTR expression persistence was observed in immunocompetent C57B1/6 mice.

Surprisingly, in the liver, E4 ORF3 alone was sufficient to promote stable and persistent expression of the transgene. The combinations of E4 ORF3+4 or E4 ORF3,6+7 also allowed for persistent gene expression. The finding that E4 ORF3 alone can rescue transgene expression in the liver, but not in the lung, indicate that tissue- or cell-type specific factors might cooperate with the E4 functions to regulate gene expression from the CMV promoter.

Taken together, our results confirm the notion that the status of the Ad E4 region regulates the expression of heterologous promoters, such as the CMV promoter, most likely by transactivation mechanism(s). In addition, our data indicate that the influence of the E4 region is complex. The E4 ORF3 is clearly required for the regulation of the CMV promoter. In the liver, the function of E4ORF3 alone is sufficient to promote persistent gene expression. In addition, the ORF 3 effect was enhanced in the presence of ORF4 or ORFs 6+7. Restoration of transgene expression in the lungs, after I.T. administration, was only obtained with the combinations E4ORF3+ORF4, or with the E4 ORFs3, 6+7. Similar results have been obtained in a second experiment wherein vector persistence and transgene expression were monitored over 3, 21, 45 and 90 days in the liver.

EXAMPLE 3

Influence of Ad5-E4 Gene Products on Late Viral Gene Expression

To monitor the effect of E4 gene products on late viral gene expression, AdE1° vectors containing individual E4 ORFs or combinations thereof were infected into A549 cells at a moi of 1000 IU/cell. As controls AdE1°E4 wt and Ad5 were similarly infected. 72 hours post infection, total messenger RNA was prepared from the infected cells and subjected to Northern blot analysis; a DNA probe specific for Hexon mRNA was used to detect viral hexon mRNA representative for late viral gene expression. The results are summarized in Table 2.

TABLE 2 late viral gene expression and transgene expression (CMV-CFTR) from E4-modified Ad vectors.

| vector | hexon mRNA | transgene expression |
| --- | --- | --- |
| Ad5 wt | +++++ | ND |
| Ad5E1°E4 wt | ++ | +++++ |
| Ad5E1°E4° | – | – |
| Ad5E1°ORF 1–4 | ++ | +++ |
| Ad5E1°ORF3,4 | ++ | +++ |
| Ad5E1°ORF3 | + | ++ |
| Ad5E1°ORF4 | – | – |
| Ad5E1°ORF6+ 7 | + | – |
| Ad5E1°ORF3,6 + 7 | +/– | +++++ |

These results demonstrate that the deletion of the entire E4 region leads to an elimination of late viral gene expression. Vectors containing E4 ORFs 1–4 or E4 ORFs 3,4 showed similar levels of late viral gene expression when compared to Ad5E1°E4 wt. Late viral gene expression was reduced in the presence of ORF3 or ORFs6+7. Interestingly, the combination of E4 ORF3 with ORFs6+7 (Ad5E1°ORF3, 6+7) lead to a further marked reduction of late viral gene expression. Importantly, the combination of E4 ORFs3,6+7 showed the highest level and persistence of transgene expression in vitro and in vivo.

This shows that such a vector, Ad5E1° containing the E4 ORFs3,6+7 does combine important features with respect to therapeutic applications: high level and persistence of transgene expression with extremely low levels of viral antigen expression and therefore low risk of immunogenicity in the host.

EXAMPLE 4

Hepatotoxicity of Adenoviral Vectors
A. Hepatotoxicity of E1-deleted Adenoviral Vectors.

Hepatotoxicity of E1-deleted adenoviral constructs was assessed in Balb/c mice and C57BL/6 mice after intravenous administration of $1.2 \times 10^{11}$ viral particles produced from empty vectors (no transgene). Pathological analysis of liver sections revealed various liver-cell damages such as hepatocellular swelling, shrinkage, acidophilic degeneration, apoptosis and mitonecrosis. No confluent necrosis was seen. Portal canaliculi were normal. The lesions were diffuse, without precise dominant localization. In combination with liver damages, numerous portal tracts were enlarged by a lymphocytic infiltration. Some foci of mononuclear cells were distributed closed to portal and centrolobular vein walls. In some experiments liver injury was apparent as early as 4 days and aggravated up to 21–30 days. Moreover, intravenous administration of E1-deleted adenovirus vectors induced elevated levels of serum transaminases (GOT, GPT), compared to control levels. In some experiments, the transaminase enhancement can be observed as early as 4–5 days after injection. The maximal is usually obtained between 14 and 21 days post-injection and is more pronounced for GPT than for GOT. GPT is a sensitive marker for hepatocellular injury and liver necrosis, whereas GOT is elevated during myocardial infarction. Values of transaminases obtained with E1-vectors confirmed hepatic injuries revealed by pathological analysis.

B. Hepatotoxicity of E4-deleted Adenoviral Vectors.

The purpose of this study is to compare the toxicity of empty doubly E1 and E4-deleted with single E1-deleted adenovirus vectors. The experiment was conducted according to the same experimental conditions as depicted above. Anatomopathological analysis of liver sections obtained from mice injected with $1.2 \times 10^{11}$ E1–E4-particles shows a reduced liver toxicity. Dystrophic lesions were sometimes seen, however clearly reduced, compared to E1-deleted adenovirus vectors. Interestingly, some lymphocytic infiltrations were observed but without inducing any dystrophic lesions.

Moreover, the concentration of GOT and GPT transaminases measured in the serum of mice injected with empty E1 and E4-deleted vectors were equivalent to background levels (controls). These results confirmed pathological observations indicating lower liver injuries when the E4 region is eliminated from the adenoviral backbone.

Accordingly, in contrast to their E1-deleted counterparts, the AdE1/E4-deleted vectors reproducibly caused a much lower toxic and inflammatory response, suggesting that E4 gene products themselves are involved in the induction of inflammatory responses.

C. Role of the Individual E4 ORFs in the Toxicity of Adenovirus Vectors.

In an effort to understand the role of E4 gene products in the toxicity of adenoviral vectors, a series of empty and isogenic vectors displaying individual or combinations of ORFs of the E4 region were designed and produced. These vectors differ from those described in Example 1 only by the absence of the CFTR expression cassette in order to eliminate transgene interference with the host immune and inflammatory responses. $2 \times 10^{11}$ particles of these constructs were injected intravenously in CBA mice to assess their liver toxicity. The results of the pathological analysis of liver sections are summarized in Table 3.

TABLE 3

Liver pathology after intravenous injections of empty E4-modified adenoviral vectors (2 mice per group per time point).

| | Day 4 p.i. | | Day 21 p.i. | |
| --- | --- | --- | --- | --- |
| E4 | Dystrophy | Inflammation | Dystrophy | Inflammation |
| E4 wild type | + | + | ++ | ++ |
| E4 deleted | – | +/– | +/– | +/– |
| ORF 6 + 7 | – | +/– | +/31 | +/– to + |
| ORF3,4 | – | +/– | +/– | +– |

TABLE 3-continued

Liver pathology after intravenous injections of empty
E4-modified adenoviral vectors (2 mice per group per time point).

| E4 | Day 4 p.i. | | Day 21 p.i. | |
|---|---|---|---|---|
|  | Dystrophy | Inflammation | Dystrophy | Inflammation |
| ORF3 | – | +/– | – | +/– |
| ORF4 | – | – | +/– | +/– to + |
| ORF3, 6 + 7 | – | – | ++ to +++ | + to ++ |

–represents no pathology whereas +++ represents many lesions and/or inflammation As previously shown, E1-deleted vectors (with a wild-type E4 region) induced dystrophy and inflammation as early as 4 days after injection and the toxicity increased 21 days post-injection. Deletion of the entire E4 region dramatically reduced this toxicity. With the exception of the vector containing ORF3, 6+7, the vectors containing individual E4ORFs and combination ORF6+7 and ORF3,4 showed reduced toxicity and inflammation, comparable to E4 deleted adenovirus vectors. In contrast, the vector containing E4 ORF3,6+7 induced hepatic dystrophy and inflammation as does an adenovirus vector retaining a wild type E4 region.

These results were completed by GOT and GPT determinations 4 and 21 days post infection. As already mentioned, injection of virions expressing wild type E4 gene products induced high levels of transaminases 21 days p.i. assessing its toxicity towards liver cells. A similar induction although slightly less pronounced is observed with E1-vectors carrying E4 ORF4 alone as well as the combination of E4 ORF3 with 6+7. In contrast, transaminase concentrations obtained with adenoviruses bearing ORF3 alone or ORFs3,4 are within the same range than those measured with controls and E1–/E4-vectors and thus can be referred to as non-toxic for liver cells. Vectors retaining ORF6+7 alone display slightly enhanced GOT and GPT serum concentrations.

In order to verify whether the toxic or non-toxic status was not a consequence of a lower input of viruses injected, viral DNA persistence was assessed in the liver by Southern blot analysis. Similar amounts of viral DNA were seen for all the vectors, suggesting that the high toxicity observed with vectors retaining a wild type E4, E4 ORF3,6+7 or E4ORF4 is an effect of some E4 gene products.

In conclusion, dissecting the E4 region and probing the E4-modified vectors for the persistence of transgene expression, in lung and liver, and their hepatotoxicity, gave rise to some unexpected results:

The combination of E4ORF3 with either E4ORF4 or E4ORF6+7 allowed persistence of transgene expression in the lung. However, the profile of transgene expression was qualitatively and quantitatively different with the different combinations. Transgene expression in the presence of the E4ORFs 3, 6+7 appeared constitutive and at even higher levels than in the presence of the wt E4 region. In contrast, transgene expression in the presence of the E4ORFs 3 and 4, although persistent, appeared to be periodically reduced and induced. Interestingly, E4ORFs3,4 vectors induced low hepatotoxicity.

In the liver, the presence of E4ORF3 was sufficient to regulate CFTR gene expression from the CMV promoter. Similarly, the combinations of E4 ORF3,4 or E4ORF6+7 allowed persistent transgene expression. Moreover, the vectors containing E4 ORF3 or E4ORF3,4 show a very low level of liver toxicity and inflammation. As these vectors combine persistent transgene expression with low toxicity, they might be useful for applications in liver specific gene therapy protocols.

What is claimed is:

1. A recombinant E1 and E3 deleted adenoviral vector comprising a gene of interest operably linked to regulatory elements, wherein said vector is further partially deleted in the E4 region and specifically retains a combination of E4 open reading frames consisting of:
   (i) ORF3, ORF6 and ORF6/7; or
   (ii) ORF3, ORF4 and ORF3/4,
   wherein said regulatory elements comprise the early cytomegalovirus promoter.

2. The vector of claim 1, wherein said retained E4 sequences are operably linked to the homologous E4 promoter.

3. The vector of claim 1, wherein said retained E4 sequences are operably linked to a heterologous promoter.

4. The vector of claim 1, wherein said retained E4 sequences comprise splicing sequences.

5. The vector of claim 1, wherein said retained E4 sequences are located in the adenoviral genome at a location different from the location where the E4 region normally resides.

6. The vector of claim 1, in which one or more viral genes of the E2 and/or the L1–L5 regions is non-functional.

7. The vector of claim 1, wherein said adenoviral vector is of human, canine, avian, bovine, murine, ovine, feline, porcine or simian origin or alternatively from a hybrid thereof.

8. The vector of claim 7, wherein said adenoviral genome is the human adenovirus 5 (Ad5) or 2 (Ad2).

9. The vector of claim 1, wherein said gene of interest is selected from the group consisting of the genes coding for a cytokine, a cell or nuclear receptor, a ligand, a coagulation factor, the CFTR protein, insulin, dystrophin, a growth factor, an enzyme, an enzyme inhibitor, an apoptosis inducer, an apoptosis inhibitor, a cytostatic agent, an apolipoprotein, an oxygen radical scavenger, a polypeptide having an anti-tumor effect, a polypeptide capable of inhibiting a bacterial, parasitic or viral infection, an antibody, a toxin, an immunotoxin and a marker.

10. The vector of claim 1, wherein said regulatory elements comprise a promoter.

11. The vector of claim 10, wherein said promoter is the early cytomegalovirus promoter or the RSV (Rous Sacoma Virus) LTR.

12. An infectious viral particle comprising the adenoviral vector of claim 1.

13. A pharmaceutical composition comprising an effective amount of the infectious viral particle of claim 12 and a pharmaceutically acceptable carrier therefor.

14. A method for preparing an infectious viral particle, comprising
   (i) introducing the vector of claim 1 into a complementation cell capable of complementing in trans said vector, to obtain a transfected complementation cell;
   (ii) culturing said transfected complementation cell under suitable conditions to permit the production of said infectious viral particle; and
   (iii) recovering said infectious viral particle from the cell culture.

15. An isolated host cell comprising the vector of claim 1.

16. A pharmaceutical composition comprising an effective amount of the adenoviral vector of claim 1 and a pharmaceutically acceptable carrier therefor.

17. A method for improving the expression and/or persistence of CFTR expression in lung tissues of a mammal, said method comprising:

constructing an adenoviral vector according to claim 1, wherein said gene of interest is the CFTR gene, and administering by aerosol, instillation, intranasal, intrapulmonary or endotracheal route a therapeutically effective amount of said adenoviral vector to a mammal in need thereof.

18. A method for improving the expression and/or persistence of expression of a gene of interest in a mammal, said method comprising:

constructing an expression vector comprising (i), said gene of interest operably linked to regulatory elements that control expression of said gene, and (ii) a polynucleotide sequence consisting of a combination of the adenoviral E4 ORF3 with at least one of the adenoviral E4 open reading frame selected from the group consisting of ORF4, ORF3/4, ORF6/7, ORF6 and ORF7, with the proviso that said expression vector does not comprise any portion of an adenovirus E3 region; and administering a therapeutically effective amount of said expression vector to a mammal in need thereof.

19. The method of claim 18, wherein said polynucleotide sequence consists of a combination of the adenoviral E4 ORF3 with the adenoviral E4 ORF4 and/or E4 ORF3/4 and wherein said expression vector does not comprise any portion of the adenovirus E3 region.

20. The method of claim 18 wherein said polynucleotide sequence consists of a combination of the adenoviral E4 ORF3 with the adenoviral E4 ORF6 and/or E4 ORF6/7 and wherein said expression vector does not comprise any portion of the adenovirus E3 region.

21. The method of claim 18, wherein said gene of interest is a gene coding for a cytokine, a cell or nuclear receptor, a ligand, a coagulation factor, the CFTR protein, insulin, dystrophin, a growth factor, an enzyme, an enzyme inhibitor, an apoptosis inducer, a cytostatic agent, an apolipoprotein, an oxygen radical scavenger, a polypeptide having an antitumor effect, a polypeptide capable of inhibiting a bacterial, parasitic or viral infection, an antibody, a toxin, an immunotoxin or a marker.

22. The method of claim 18, wherein said regulatory elements comprises the early cytomegalovirus promoter.

23. The method of claim 18, wherein said regulatory elements comprises the RSV (Rous Sarcoma Virus) LTR.

24. A method for improving the expression and/or persistence of expression of a gene of interest in a mammal, said method comprising:

constructing an E1 and E3 deleted adenoviral vector comprising said gene of interest, operably linked to regulatory elements that control expression of said gene, wherein said adenoviral vector is further deleted in the E4 region but retains E4 ORF3 and at least one of the E4 adenoviral open reading frame selected from the group consisting of ORF4, ORF3/4, ORF6/7, ORF6 and ORF7, and administering a therapeutically effective amount of said adenoviral vector to a mammal in need thereof.

25. The method of claim 24, wherein said E1 and E3 deleted adenoviral vector retains E4 ORF3 with E4 ORF4 and/or ORF3/4.

26. The method of claim 24, wherein said E1 and E3 deleted adenoviral vector retains E4 ORF3 with ORF6 and/or ORF6/7.

27. The method of claim 24, wherein said adenoviral vector is further deleted in the E2 and/or the L1–L5 regions.

28. The method of claim 24, wherein said gene of interest is a gene coding for a cytokine, a cell or nuclear receptor, a ligand, a coagulation factor, the CFTR protein, insulin, dystrophin, a growth factor, an enzyme, an enzyme inhibitor, an apoptosis inducer, a cytostatic agent, an apolipoprotein, an oxygen radical scavenger, a polypeptide having an antitumor effect, a polypeptide capable of inhibiting a bacterial, parasitic or viral infection, an antibody, a toxin, an immunotoxin or a marker.

29. The method of claim 24, wherein said regulatory elements comprises the early cytomegalovirus promoter.

30. The method of claim 24, wherein said regulatory elements comprises the RSV (Rous Sarcoma Virus) LTR.

31. A method for improving the expression and/or persistence of expression of a gene of interest in lung tissues of a mammal, said method comprising:

constructing an expression vector comprising (i) said gene of interest, operably linked to regulatory elements that control expression of said gene into said tissue, and (ii) a polynucleotide sequence consisting of a combination of the adenoviral E4 ORF3 with the adenoviral E4 open reading frames ORF6 and/or ORF6/7 or ORF4 and/or ORF3/4 or ORF1, ORF2 and ORF4, said recombinant vector does not further comprise any portion of an adenovirus E3 region, and administering a therapeutically effective amount of said expression vector to a mammal in need thereof.

32. The method of claim 31, wherein said polynucleotide sequence consists of a combination of the adenoviral E4 ORF3 with the adenoviral E4 ORF4 or ORF6/7 and wherein said expression vector does not comprise any portion of the adenovirus E3 region.

33. The method of claim 31, wherein said expression vector is administered to said mammal by the intrapulmonary or intratracheal route.

34. The method of claim 31, wherein said regulatory elements comprises the early cytomegalovirus promoter.

35. The method of claim 31, wherein said regulatory elements comprises the RSV (Rous Sarcoma Virus) LTR.

36. A method for improving the expression and/or persistence of expression of a gene of interest in lung tissues of a mammal, said method comprising:

constructing an E1 and E3 deleted adenoviral vector comprising said gene of interest, operably linked to regulatory elements that control expression of said gene, wherein said adenoviral vector is partially deleted in the E4 region but specifically retains E4 ORF3 and further E4 open reading frames ORF4 and ORF3/4, or ORF6 and ORF6/7, and administering a therapeutically effective amount of said adenoviral vector to a mammal in need thereof, wherein said regulatory elements comprise the early cytomegalovirus promoter.

37. The method of claim 36, wherein said E1 and E3 deleted adenoviral vector retains E4 ORF3 with EF ORF4 or ORF6/7.

38. The method of claim 36, wherein said adenoviral vector is further deleted in the E2 and/or the L1–L5 regions.

39. The method of claim 36, wherein said regulatory elements comprises the early cytomegalovirus promoter.

40. The method of claim 36, wherein said regulatory elements comprises the RSV (Rous Sarcoma Virus) LTR.

41. A method for improving the expression and/or persistence of expression of a gene of interest in the liver tissue of a mammal, said method comprises:

constructing an expression vector comprising (i) said gene of interest, operably linked to regulatory elements that control expression of said gene into said tissue, and (ii) a polynucleotide sequence consisting of a combination of the adenoviral E4 ORF3 with the adenoviral E4 open reading frames ORF4 and/or ORF314 with the proviso that said expression vector does not comprise any portion of the adenovirus E3 region, and administering a therapeutically effective amount of said expression vector to a mammal in need thereof.

42. The method of claim 41, wherein said expression vector is administered to said mammal by the intravenous route.

43. The method of claim 41, wherein said regulatory elements comprises the early cytomegalovirus promoter.

44. The method of claim 41, wherein said regulatory elements comprises the RSV (Rous Sarcoma Virus) LTR.

45. A method for reducing hepatotoxicity in a mammal subsequent to the administration to said mammal of an E1 and E3-deleted adenoviral vector comprising a gene of interest placed under the control of the early cytomegalovirus promoter, wherein said adenoviral vector is further partially deleted in the E4 region and specifically retains the adenoviral E4 open reading frame:

(i) ORF3, or
(ii) ORF3, ORF4 and ORF3/4, wherein hepatotoxicity following administration of said adenoviral vector is reduced in comparison to that observed following administration of an adenoviral vector comprising the complete E4 region.

46. The method of claim 45, wherein said adenoviral vector is further deleted in the E2 and/or the L1–L5 regions.

47. The method of claim 45, wherein said adenoviral vector is administered to said mammal by intravenous route.

48. A method for improving the expression and/or persistence of expression of a gene of interest in the liver tissue of a mammal, said method comprises:

constructing an E1 and E3 deleted adenoviral vector comprising said gene of interest, operably linked to regulatory elements that control expression of said gene, wherein said adenoviral vector is further deleted in the E4 region but specifically retains E4 ORF3 with E4 ORF4 and ORF3/4, administering a therapeutically effective amount of said adenoviral vector to a mammal in need thereof, wherein said regulatory elements comprise the early cytomegovirus.

49. The method of claim 48, wherein said adenoviral vector is further deleted in the E2 and/or the L1–L5 regions.

50. The method of claim 48, wherein said regulatory elements comprises the early cytomegalovirus promoter.

51. The method of claim 48, wherein said regulatory elements comprises the RSV (Rous Sarcoma Virus) LTR.

52. The method of claim 48, wherein said adenoviral vector is administered to said mammal by intravenous route.

* * * * *